(12) United States Patent
Zia et al.

(10) Patent No.: US 6,508,859 B1
(45) Date of Patent: Jan. 21, 2003

(54) METHOD AND APPARATUS FOR REMOVING AIR OR GAS FROM FLUID

(75) Inventors: Majid Zia, White Bear Township, MN (US); Eric M. Hollnagel, Shoreview, MN (US); Craig J. Cuta, White Bear Lake, MN (US)

(73) Assignee: Porous Media Corporation, St. Paul, MN (US)

( * ) Notice: Subject to any disclaimer, the term of this patent is extended or adjusted under 35 U.S.C. 154(b) by 34 days.

(21) Appl. No.: 09/711,638

(22) Filed: Nov. 13, 2000

(51) Int. Cl.[7] .............................................. B01D 19/00
(52) U.S. Cl. ............................... 95/46; 95/241; 95/254; 96/6; 96/179; 96/219; 210/188; 604/4
(58) Field of Search ........................... 95/46, 241, 262, 95/254; 96/6, 155, 219, 220, 179; 210/188; 604/4, 405, 406

(56) References Cited

U.S. PATENT DOCUMENTS

| | | | |
|---|---|---|---|
| 3,295,297 A | * | 1/1967 | Collins |
| 3,803,810 A | * | 4/1974 | Rosenberg |
| 4,177,149 A | * | 12/1979 | Rosenberg |
| 4,190,426 A | * | 2/1980 | Ruschke |
| 4,278,084 A | * | 7/1981 | Pope, Jr. |
| 4,294,594 A | * | 10/1981 | Sloane, Jr. et al. |
| 4,298,358 A | | 11/1981 | Ruschke |
| 4,326,957 A | * | 4/1982 | Rosenberg |
| 4,341,538 A | * | 7/1982 | Vadnay et al. |
| 4,525,182 A | * | 6/1985 | Rising et al. |
| 4,601,712 A | | 7/1986 | Cole et al. |
| 4,900,308 A | | 2/1990 | Verkaart |
| 4,906,260 A | * | 3/1990 | Emheiser et al. |
| 5,252,222 A | * | 10/1993 | Matkovich et al. |
| 5,439,587 A | * | 8/1995 | Stankowski et al. |
| 5,707,520 A | * | 1/1998 | Kuroki et al. |
| 5,779,674 A | | 7/1998 | Ford |
| 5,827,429 A | * | 10/1998 | Ruschke et al. |
| 5,849,065 A | | 12/1998 | Wojke |

OTHER PUBLICATIONS

"Jet Reattachment and the Coanda Effect" of the chapter entitled "Jets, Plumes, Wakes, and Shear Layers" from the Applied Fluid Dynamics Handbook, Krieger Publishing Co. (1992).

* cited by examiner

Primary Examiner—Duane S. Smith
(74) Attorney, Agent, or Firm—Marshall & Melhorn, LLC

(57) ABSTRACT

A device for removing entrained air or gas from fluids includes a first chamber having a fluid inlet and an outlet, a second chamber, adjacent said first chamber, having a plurality of channels, a porous barrier separating the first chamber and the second chamber and a vent in fluid communication with the second chamber. The inlet is connected to the first chamber through at least one fluid passage. Fluid flows from the inlet, through the passage, and into the first chamber. A fluid dead zone adjacent the barrier assists an air or gas bubble to coalesce and pass through the barrier into the second chamber. The plurality of channels within the second chamber collect the air or gas and direct it to the vent in communication with the channels. A clip, or similar device, may be used to secure the device to medical equipment adjacent the patient or fluid source.

57 Claims, 11 Drawing Sheets

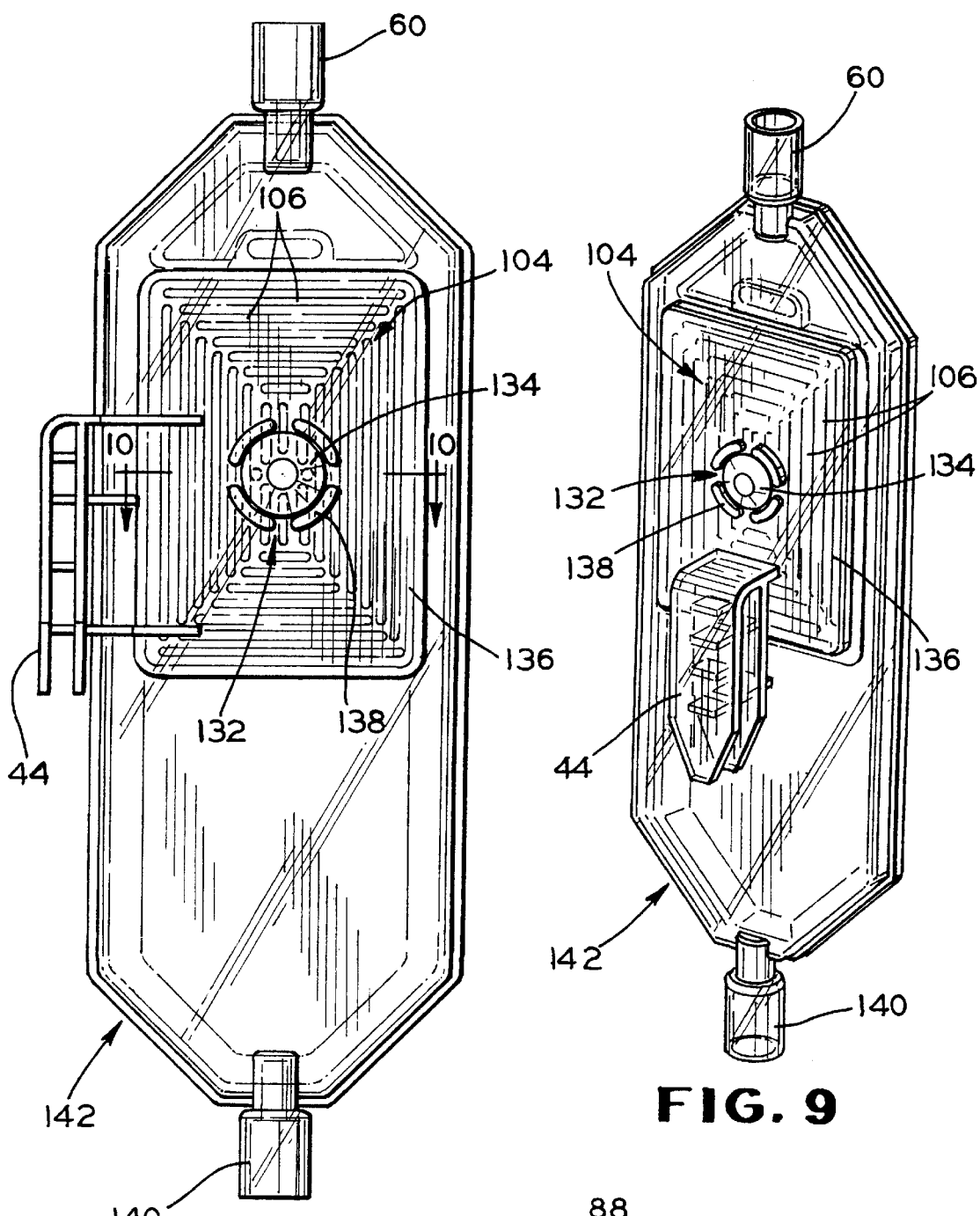
FIG. 8
FIG. 9
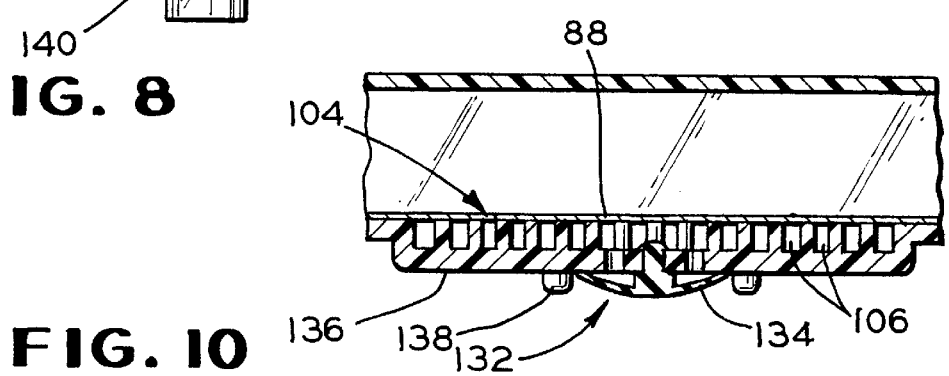
FIG. 10

US 6,508,859 B1

METHOD AND APPARATUS FOR REMOVING AIR OR GAS FROM FLUID

BACKGROUND OF THE INVENTION

The present invention relates to a device for separating and removing air or gas from fluids for intravenous infusion into a patient. Most particularly, the invention relates to a device for separating and removing air or gas from fluids processed through pressure infusion systems and fluid warming devices before parenteral infusion into a patient.

DISCUSSION OF THE RELATED ART

U.S. Pat. No. 4,298,358 shows a fluid filter which separates gas from liquid and vents the separated gas from the filter. The filter includes a vented housing through which the fluid stream passes. Liquid-wetting filter means carried in the housing in the path of the fluid stream permits the passage of liquid only. Gas separated from the fluid is vented through vent opening means which is covered by a liquid-repellent filter to permit the passage of gas only. An automatic pressure sensitive control means may be used to seal the vent opening means against the entry of ambient air but to automatically release separated gas from the filter. The liquid-repellent filter may be secured to the housing by a mechanical bond between the housing and a fibrous backing carried by the filter, or a continuous band of medical grade tape may be used to attach the filter to the housing.

U.S. Pat. No. 4,601,712 shows an improved conduit communicating between a pressurized source of solution and a partially filled reservoir associated with a drip chamber in a continuous-flush system. The conduit comprises a tube that is bent at approximately a 45 degree angle so that solution discharging from the conduit is diverted to impinge against the interior wall of the reservoir before interfacing with the solution accumulated therein. The arrangement reduces bubble formation normally associated with turbulent discharge flow during filling and flushing of the system.

The device shown in U.S. Pat. No. 4,601,712 works satisfactorily. The entrained bubbles of air or gas do come out of the fluid faster that with other drip chambers. However, the impingement of the fluid against the wall of the device, while alleged to reduce turbulence associated with turbulent discharge flow, still produces a level of turbulence which is felt to be unsatisfactory to those skilled in the art. In addition, the drip chamber disclosed has no vent, and thus there exists the need to turn the device over to vent it.

U.S. Pat. No. 4,900,308 shows an air elimination device which includes a plenum arranged to cause a reduction in flow velocity of a physiological fluid whereby air bubbles form and rise to the top of the plenum. A hydrophobic membrane covers the top of the plenum, and the pressure in the fluid is greater than that which is required to drive the released air through the membrane and into the atmosphere. The air which collects at the top of the plenum forms a protective surface on the bottom of the hydrophobic membrane to prevent its being clogged by cellular materials. A support stand engages the air eliminator to hold it in the desired orientation whereby the air bubbles form at the top of the plenum.

While the device disclosed works well enough in continuous use, it has been found by those skilled in the art that the device may not work well in intermittent flow conditions. This is due to repeated membrane exposure to blood products. This has been found to cause clogging because the bubble layer in the device does not stay in place once fluid flow stops. When this occurs, the membrane will be contacted by cellular products when flow resumes, and will become clogged.

U.S. Pat. No. 5,779,674 shows a fluid gas removal drip chamber for use for parenteral administration of fluids is disclosed. The drip chamber has a hydrophobic barrier which extends into the interior of the drip chamber. The hydrophobic barrier preferably comprises at least a portion of a three-dimensional surface. In one embodiment, an inlet port allows fluid to enter the drip chamber from the top so that the fluid falls through an air space formed in the top of the drip chamber. By shaping the inlet port so that droplets of fluid are formed, a health care professional can monitor the fluid drip rate. In another embodiment, the hydrophobic barrier is configured so that little or no air space exists at the top of the drip chamber. The drip chamber includes means for venting air that is separated from the fluid within the chamber and at the same time preventing air from entering the chamber through the venting means. For certain applications, the drip chamber is provided with a hydrophilic filter for filtering the fluid prior to exiting the drip chamber. This device works satisfactorily under continuous and intermittent flow conditions, but requires a complicated and expensive support for the hydrophobic barrier used therein, and thus, is not cost effective.

Pressure infusion systems may deliver fluid at a rate which is too fast for the body to adequately warm, thereby increasing the risk of hypothermia. Therefore, fluid warming devices may be connected to the pressure infusion system to warm the intravenous fluids to body temperature (about 37° C.) before infusion into the patient. However, warming the fluid, among other things, may encourage any air or gas bubbles entrained, or within the system, to travel with the fluid. It is well understood in the art that air or gas bubbles should be prevented from entering into the blood stream of a patient. Air or gas which does enter a patient's blood stream may result in an embolism.

In the prior art, there are a number of devices for removing air or gas bubbles from intravenous fluid. One category of such devices is the drip chamber. In the drip chamber, the bubbles and the fluid are separated by dripping the fluid onto a fluid-gas interface. Gas is trapped in an unvented reservoir while the fluid is allowed to exit the reservoir. Traditionally, drip chamber devices are not well-suited for high fluid flow applications due to their limited volumetric capacity and due to excessive gas bubble creation at the fluid-gas interface. Often, the resulting excessive bubbles are not retained in the reservoir, but instead are allowed to escape through the outlet. Further, because of its limited volumetric capacity, a drip chamber is limited in the amount of air that can be processed, and must be inverted periodically to vent the air removed.

A second category of fluid-gas separation devices is a filter where the fluid passes through a filter medium that positively stops the passage of bubbles. Such filter mediums, however, may impede the flow of certain fluids through the device, including drugs being administered. Filter media are also prone to blockages that may result in a complete stoppage of fluid flow. Furthermore, when filter media are used for blood or blood products the fragility of the cells may limit the range of operating conditions of the device.

A third category of fluid-gas separation devices employs a hydrophobic barrier to allow air or gas within the fluid to pass through the barrier and escape to a vent. Although the barrier allows air or gas within a liquid to escape, the barrier prevents the liquid itself from escaping. Further, when the hydrophobic barrier is in the form of a tube, such as in the aforementioned U.S. Pat. No. 5,779,673, such fluid-gas separation devices are not cost effective.

Thus, none of the above-described devices are entirely suitable for high volume, high flow separation of air or gas from biological fluids such as saline, air, or blood on a continuous basis, such as is required by modern pressure infusion systems. It was desired, for example, to develop a device capable of venting a single 2 ml air bolus while infusing 20 ml of fluid As discussed above, the devices presently available can not do this on a continuous basis, or can not do so without developing serious operational problems. Thus, those skilled in the art continued to search for a satisfactory high flow separation device.

The present invention provides an effective, low cost device for removing air or gas bubbles from fluids prior to intravenous infusion into a patient. The invention is particularly well-suited for intermittent, or continuous gas bubble separation from solutions such as blood, blood products, saline or other biological fluids. The present invention is especially suitable for use at high fluid flow rates, where endurance and large venting capability is desired, such as during surgery, where the high flow separation device of the present invention may be used on a continuous or intermittent basis for up to four hours, or up to ten (10) units of blood. Additionally, the present invention has few parts, is easily manufactured and assembled, has exceptional durability when exposed to cellular components, and is low in cost when compared to existing devices.

SUMMARY OF THE INVENTION

The invention is a device for removing gas or air from fluids used in fluid warming devices before intravenous delivery to a patient. Fluid enters the device through at least one inlet. At least one passage directs the fluid from the inlet into a first chamber.

Fluid enters the chamber along the sidewalls thereof to create a smooth entrance into the chamber. It is desired that the fluid being processed does not "splash" into the chamber, but remains attached to, or reattaches itself to the sidewalls as it enters the first chamber. The smooth entrance of the fluid into the chamber also helps to create a fluid dead zone adjacent the porous barrier which assists the coalesced air or gas to pass through the barrier into second chamber.

The fluid "dead zone" is a zone within the first chamber where the fluid velocity is minimal or substantially non existent. There is no downward force on the gas bubbles, and the bubbles quickly rise and coalesce. This results in a more effective and expedited removal of any entrained gas. This, in turn, results in a substantially smaller housing design.

A plurality of interconnected channels within the second chamber collects and transports the air or gas to a vent. Gas re-introduction into the invention is prevented by locating a check valve downstream of the vent. Additionally, the outlet may be sized such than an appropriate back-pressure is created to prevent gas re-introduction into the device. In addition to the first chamber barrier, a porous barrier, preferably hydrophillic, may also be placed in the chamber upstream of the outlet to prevent the inadvertent passage of minor gas bubbles through the exit. If desired, such a barrier may be liquid wetting, and of an appropriate pore size to provide an automatic shut off if more air enters the system than desired. A clip, or similar means, may be used to secure the device to medical equipment adjacent the patient or fluid source.

BRIEF DESCRIPTION OF THE DRAWINGS

FIG. 8 shows a further modification of the construction shown in FIG. 2, having a side-mounted attachment clip and a diaphragm vent.

FIG. 9 is a view similar in part to FIG. 8 but showing the attachment clip located on the second wall below the diaphragm vent.

FIG. 10 is a sectional view, taken in the direction of the arrows, along the section line 10—10 of FIG. 8.

DETAILED DESCRIPTION OF THE PREFERRED EMBODIMENTS

It is to be understood that the specific structures and processes illustrated in the attached drawings, and described in the following description, are simply exemplary embodiments of the inventive concepts defined in the appended claims. Hence, specific dimensions and other physical characteristics relating to the embodiments disclosed herein should not be considered as limiting, unless the claims expressly state otherwise.

Figure 1:
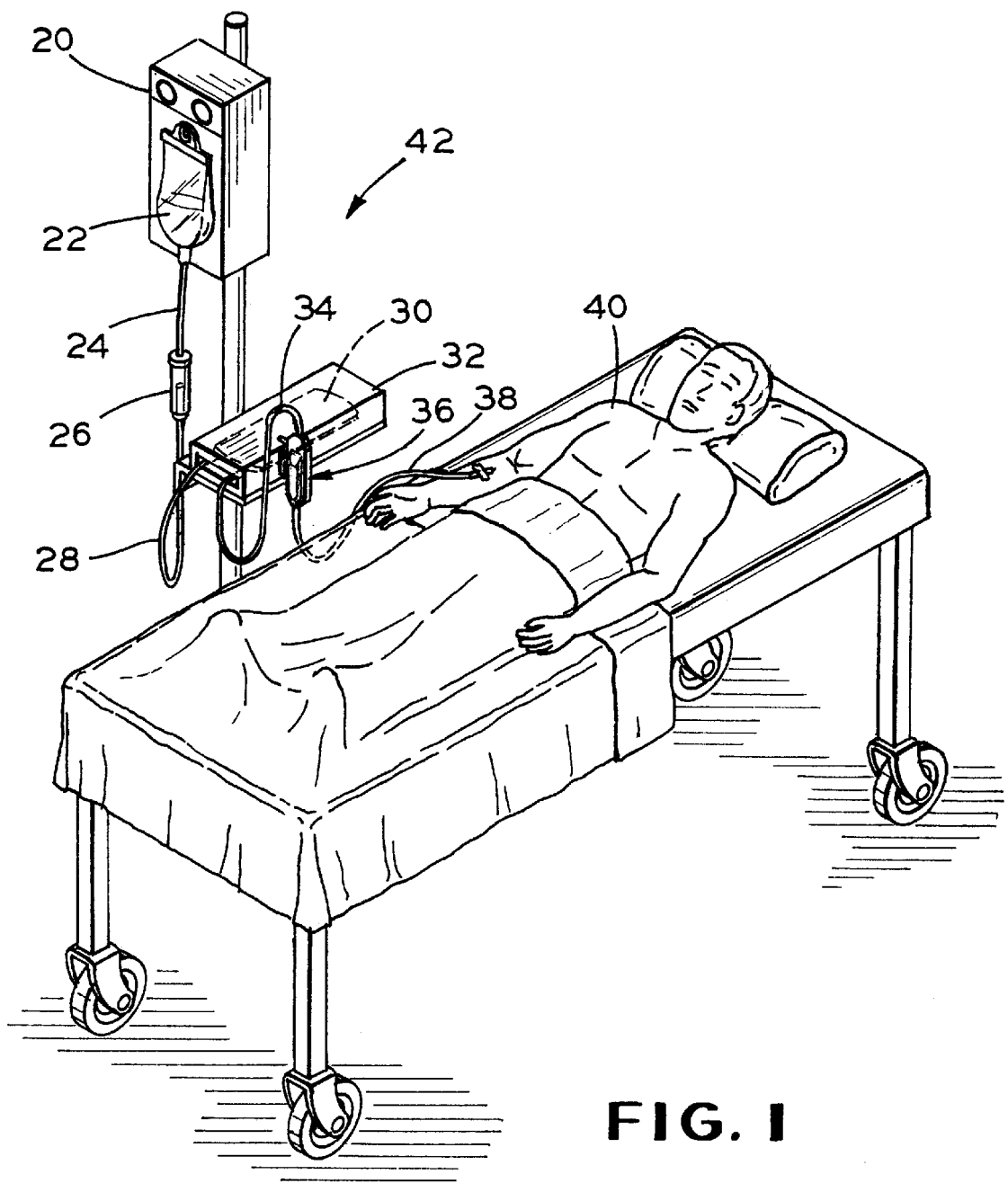
FIG. 1 depicts the invention connected in series in a fluid delivery system including a fluid pressure infusion system, a fluid warming system, the present invention and a patient recipient of the pressurized, warmed and filtered fluid.

Referring now to FIG. 1, there is shown a pressure infusion system 20 in combination with a fluid source, such as an IV bag 22. The IV bag 22 may be mounted to the pressure infusion system 20. The pressure infusion system 20 can be such as the Model No. H25 manufactured by Level 1 Technologies of Marshfield, Mass. 02050 U.S.A. The IV bag 22 is in fluid communication typically through surgical tubing 24, with a drip chamber 26. Drip chambers 26 are well-known in the art and typically contain a fine mesh or screen in the fluid path for removing microaggregate blood clots and the like from the fluid. The drip chamber 26 is connected in series by surgical tubing 28 to a fluid warming bag 30. The fluid warming bag 30 may be such as the Model No. 24350, manufactured by Augustine Medical of Eden Prairie, Minn.

The fluid warming bag 30 may be used in combination with a fluid warming system 32. The fluid warming system 32 may be such as the Ranger Fluid Warmer Model No.245, manufactured by Augustine Medical, Inc. of Eden Prairie, Minn. 55344. The fluid is transferred from the fluid warming system 32, typically by surgical tubing 34, to the high flow separation device 36, also known as a bubble trap 36, where the air and gas bubbles are removed. Fluids, having any air or gas removed from them, may then be administered to a patient 40 by connecting the high flow separation device 36, such as by surgical tubing 38, in fluid communication with the patient 40.

Figure 2:
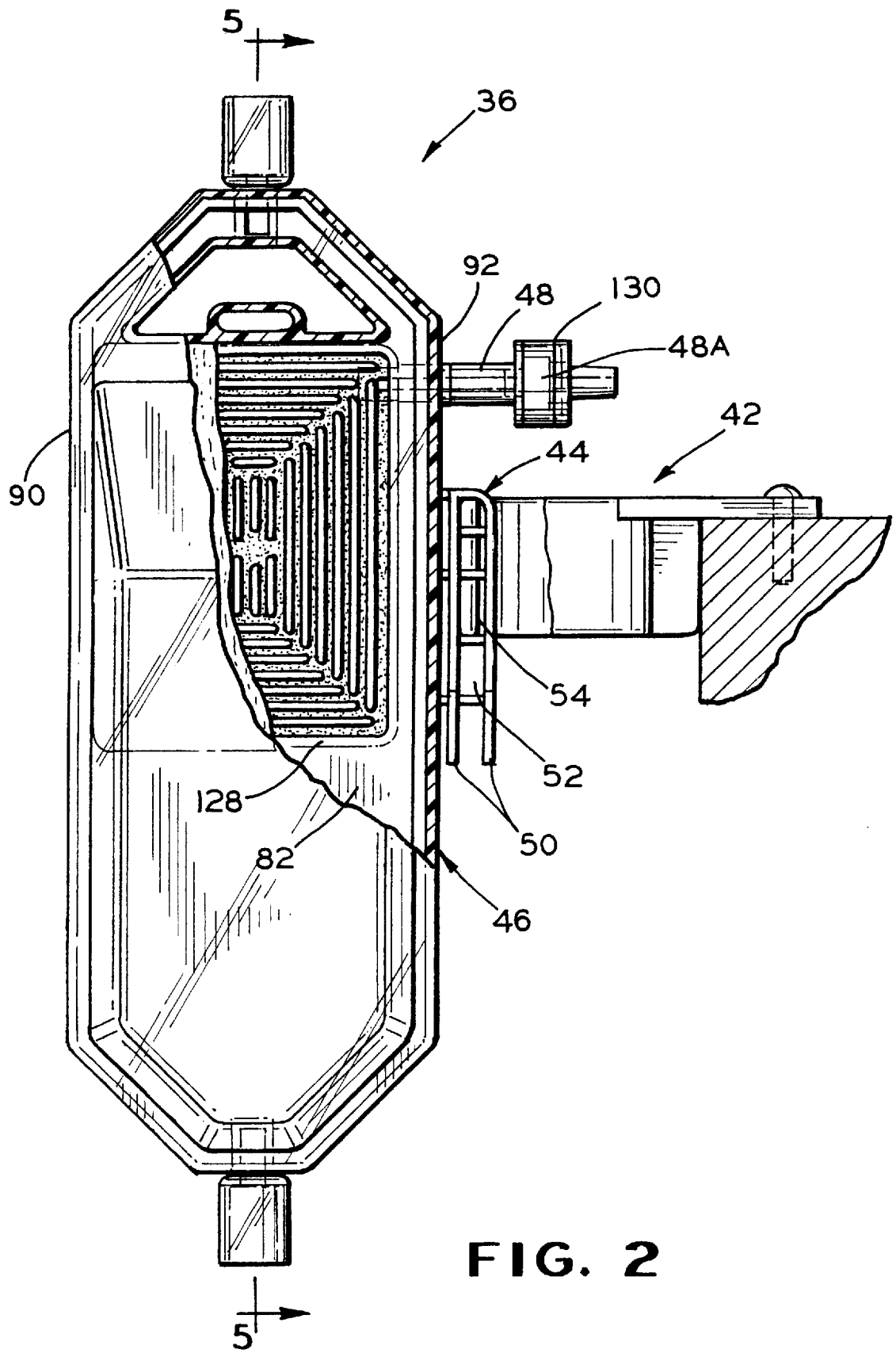
FIG. 2 is a partial sectional view of the invention depicting a faceted fluid passage and a side-mounted attachment clip. The attachment clip is, in turn, shown connected to the fluid warming system.

Referring now to FIG. 2, a means for easily attaching and detaching the high flow separation device 36 to and from medical equipment 42 adjacent the patient 40 and/or the fluid source 22 is depicted. The attachment means is designed to maintain the high flow separation device 36 in a substantially upright attitude while in use. As depicted in FIG. 2, the attachment means is preferably a clip 44. FIG. 2 depicts one embodiment of the clip 44 wherein the clip 44 is integrally formed with a side wall 46 adjacent a vent 48. Check valve 48A may be attached to vent 48. The clip 44 is preferably of a double wall construction wherein the double walls 50 are separated by a plurality of engagement channels 52. The engagement channels 52 are for engagement and disengagement with corresponding supportive elements 54 from adjacent equipment 42. The engagement channels 52 securely engage the supportive elements 54 from the adjacent equipment 42 to prevent inadvertent displacement of the high flow separation device 36 during use.

Figure 3:
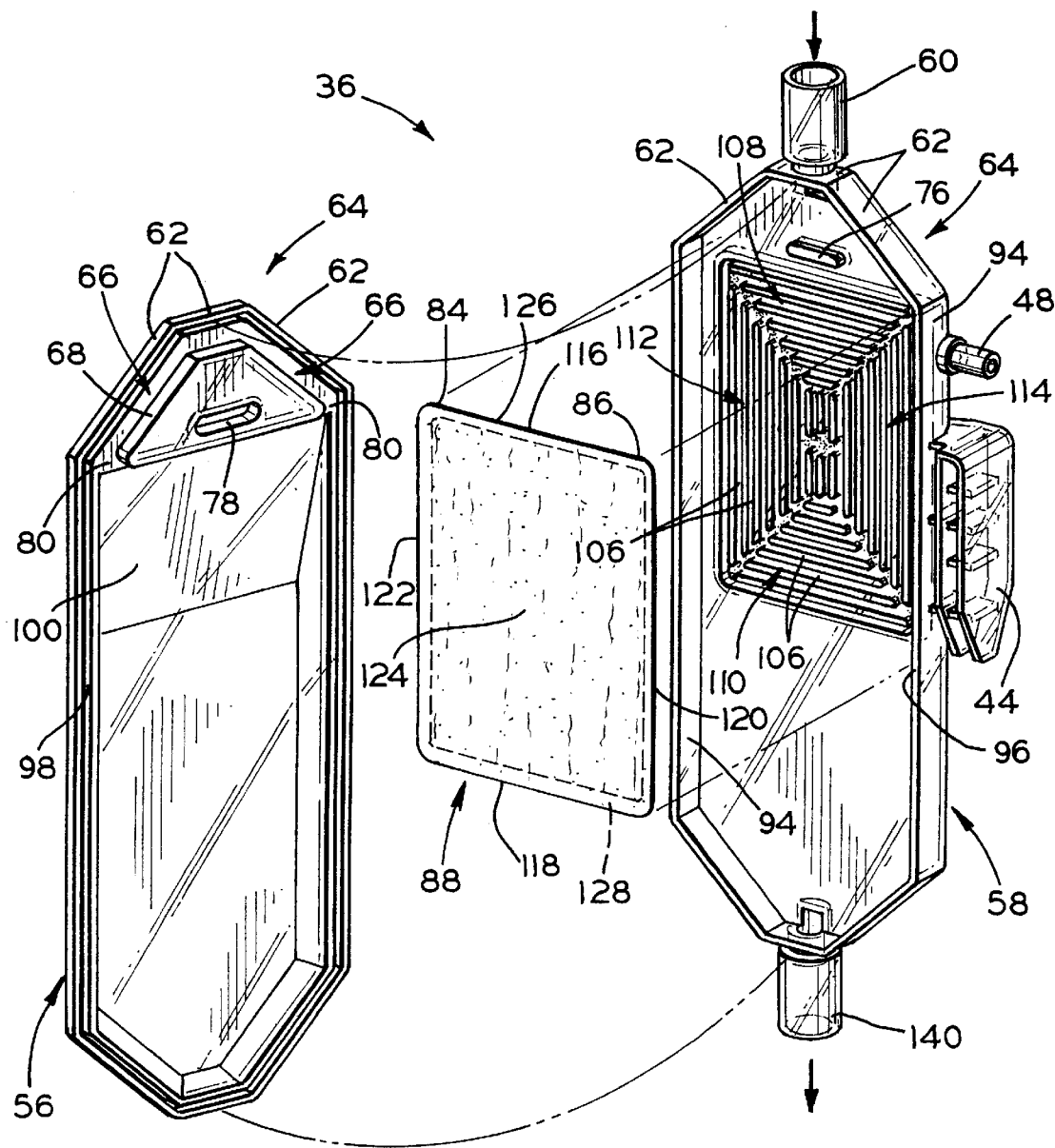
FIG. 3 is an exploded view of the faceted fluid passage embodiment of the invention.

Referring now to FIG. 3, a first wall 56 and a second wall 58 of the high flow separation device 36 are depicted. A fluid inlet 60 is integrally formed with the second wall 58. Although the high flow separation device 36 has been described with the inlet 60 being integrally formed with the second wall 58, it may be readily appreciated that the inlet 60 may also be formed with the first wall 56 without departing from the scope or spirit of the high flow separation device 36.

The inlet 60 acts to communicate fluids from a fluid source 22 (see FIG. 1) to the interior of the high flow separation device 36. Surgical tubing is used to connect the inlet 60 with the fluid source 22. See FIG. 1 The surgical tubing is fixedly attached to the inlet 60 by means well known in the art, such as solvent bonding, adhesive bonding, or any other practical method known in the art.

In an alternative embodiment, more than one inlet may be used to communicate fluids from a fluid source 22 to the interior of the high flow separation device 36 (not shown). Multiple inlets allow for an increased fluid flow into the interior of the high flow separation device 36 thereby allowing a larger volume of fluid to be processed. Each of the plurality of inlets may be connected to a fluid source 22, or sources, in substantially the same manner as described above.

In a preferred embodiment, the inlet 60 is integrally formed with a multi-faceted 62, or multi-surfaced, inlet end 64. Each of the facets 62 is an angled flow surface designed to direct the incoming fluid into at least one flow passage 66. The passage 66 is formed by a plurality of down standing walls 68 extending from the first wall 56 proximate the inlet end 64 in the direction of the second wall 58. The down standing walls 68 extend in a substantially parallel, spaced-apart relationship to the angled surfaces 62 of the inlet end 64. The spaced-apart relationship between the down standing walls 68 and the angled surfaces 62 creates at least one passage 66 proximate the inlet 64 into which fluid flowing from the inlet 60 is directed. In the most preferred embodiment, the fluid is directed into two fluid passages 66 formed in the manner described above.

In an alternative embodiment, at least one passage 66 may be formed by a plurality of upstanding walls extending from the second wall 58 proximate the inlet 64 in the direction of the first wall 56 (not shown). The upstanding walls extend in a substantially parallel, spaced-apart relationship to the angled surfaces 62 of the inlet end 64. The spaced-apart relationship between the upstanding walls and the angled surfaces 62 creates at least one passage 66 proximate the inlet end 64 into which fluid flowing from the inlet 60 is directed.

In an alternative embodiment, more than two passages direct fluid from the inlet 60 into the interior of the high flow separation device 36 (not shown). The passages may be formed by a plurality of down standing walls extending from the first wall 56 proximate the inlet end 64 in the direction of the second wall 58, or vice versa. In the most preferred embodiment, the down standing walls are in a substantially parallel, spaced-apart relationship to each other, thereby forming the passages. The passages are formed not only between the down standing walls and the angled surfaces 62, but also between adjacent down standing walls. The plurality of passages allows a greater volume of fluid to flow from the inlet 60 into the interior of the high flow separation device 36.

Figure 4:
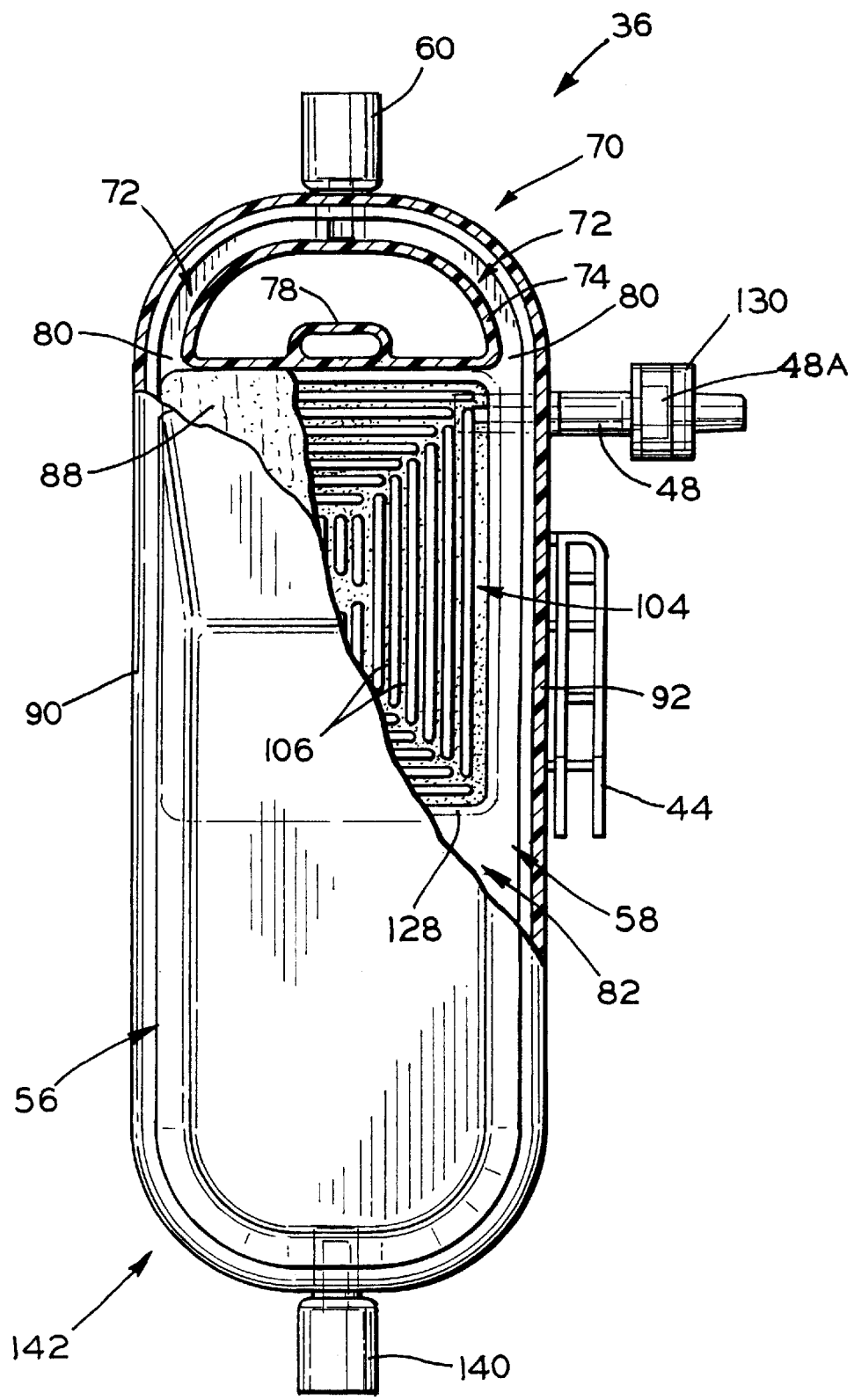
FIG. 4 is a partial sectional view of an alternative embodiment of the invention depicting an elliptical fluid passage.
Figure 5:
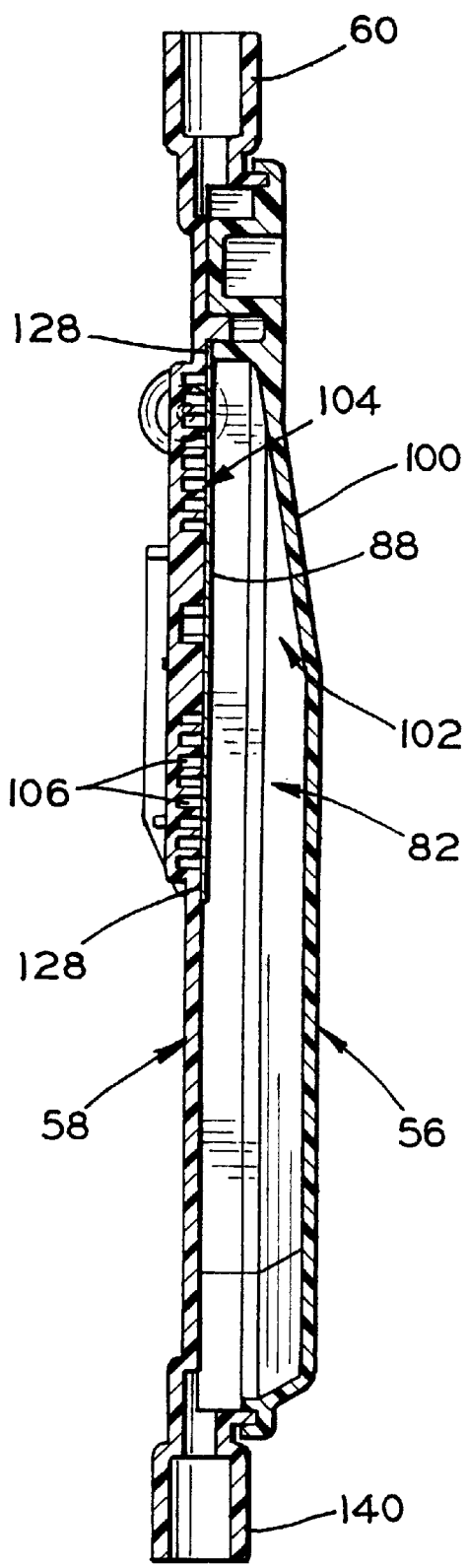
FIG. 5 is a sectional view, taken in the direction of the arrows, along the section 5—5 of FIG. 2.

FIG. 4 depicts yet another embodiment of the high flow separation device 36 wherein the inlet end 70 is elliptical, rounded, oval, U-shaped, or curvilinear. At least one elliptical down standing wall 74 extends from the second wall 58 to the first wall 56 in a substantially parallel, spaced-apart relationship to the elliptical inlet end 70. The spaced-apart relationship between the elliptical down standing wall 74 and the elliptical inlet end 70 creates at least one passage proximate the inlet 70 into which fluid flowing from the inlet 60 is substantially directed.

In the most preferred embodiment, depicted in FIG. 4, at least two passages 72 are created between the elliptical inlet end 70 and the substantially parallel down standing wall 74. It can also be appreciated that the passages 72 may be created between the elliptical inlet end 70 and at least one upstanding wall without departing from the scope or spirit of the invention (not shown)

In alternative embodiments, the inlet end 70 may also be parabolic, U-shaped, circular, or rounded, without departing from the scope or spirit of the invention. In these embodiments, spaced-apart down standing 74 or upstanding walls may be located in a substantially parallel relationship to the inlet end 70 to form the fluid passages 72 described above Other embodiments of the above device are well within the scope of the present invention.

Figure 13:
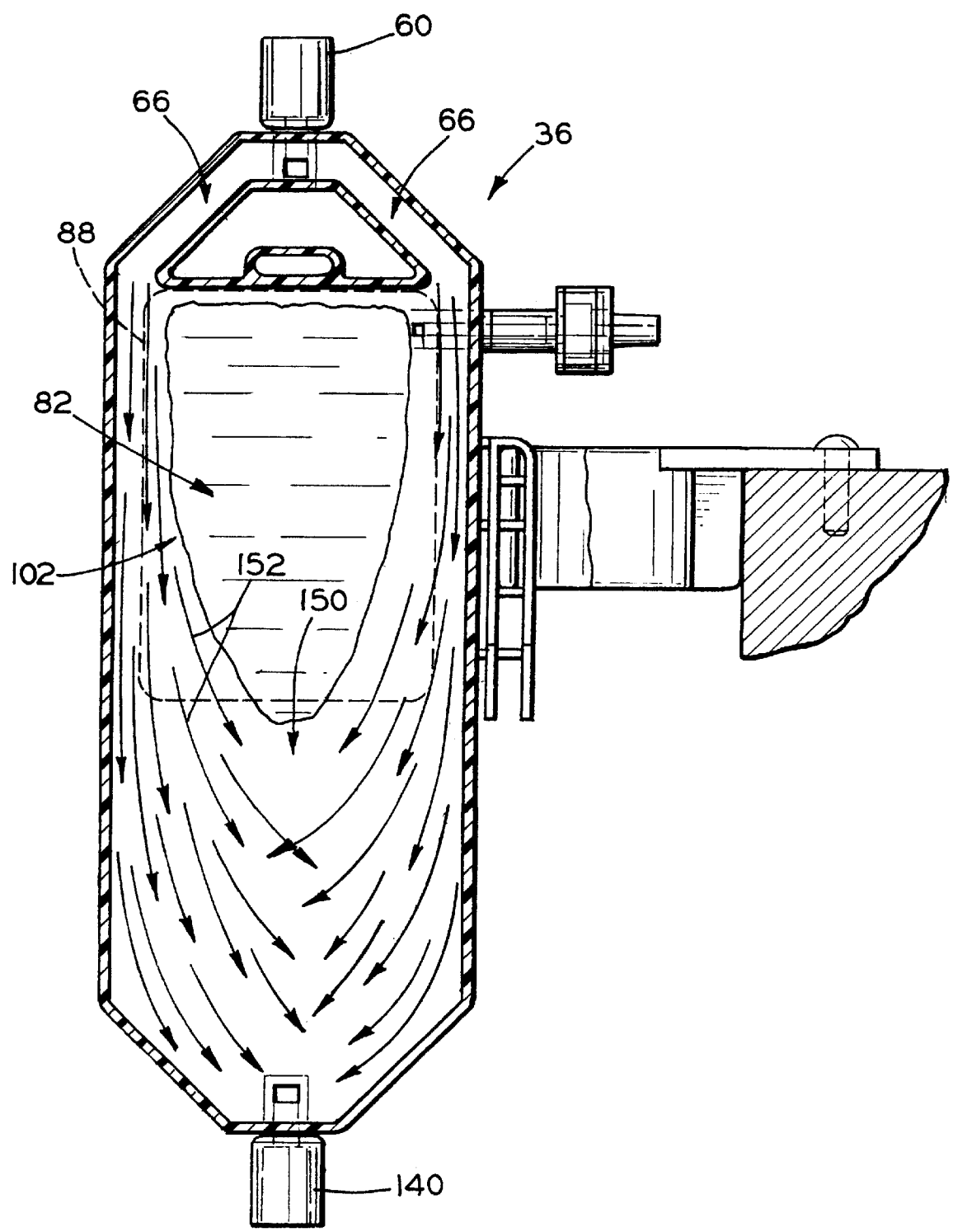
FIG. 13 is a view, similar in part to FIG. 2, showing flow through the high flow separation device embodying the present invention under "low flow" conditions, and the resulting "dead zone".
Figure 14:
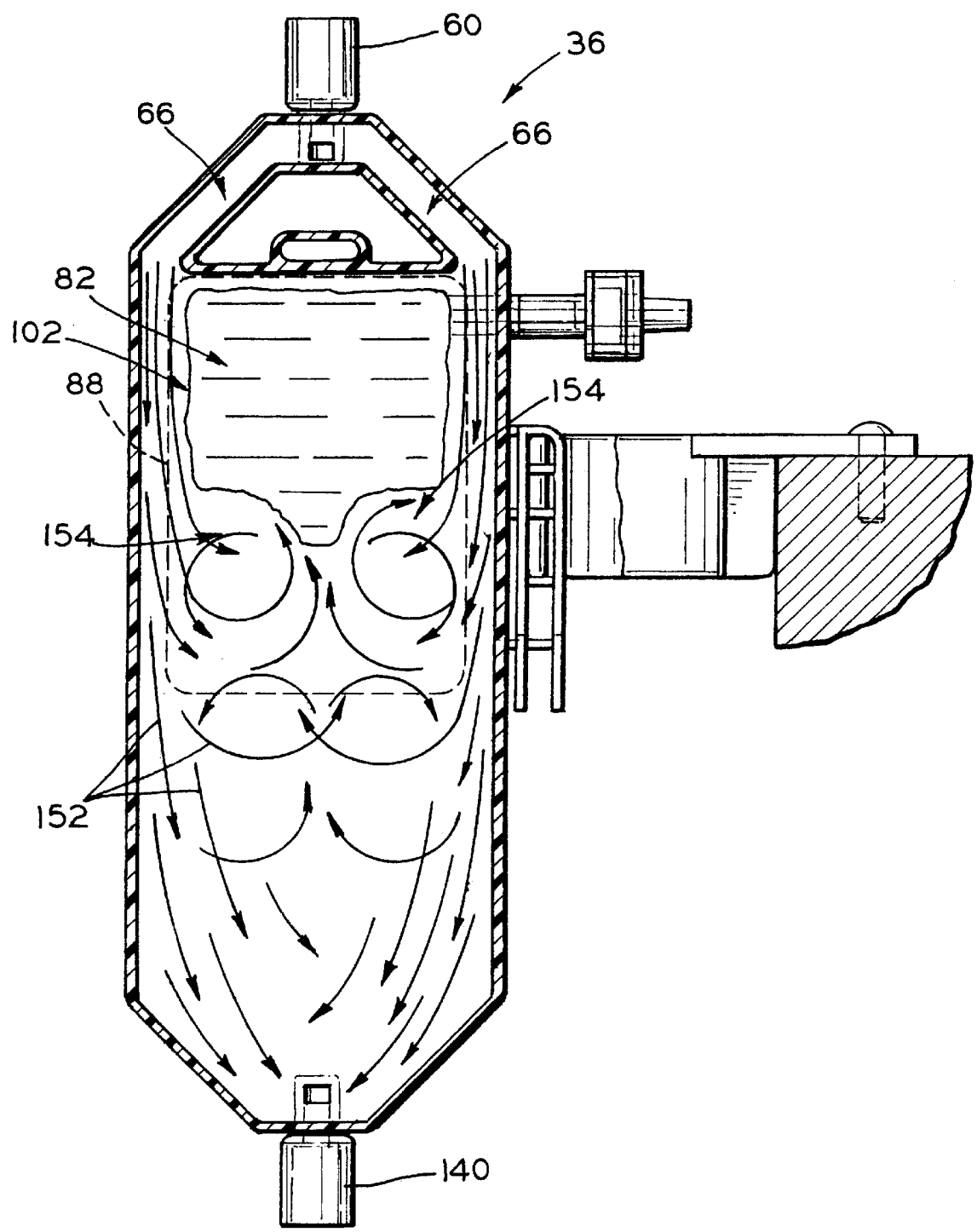
FIG. 14 is a view, similar in part to FIG. 13, showing flow through the high flow separation device embodying the present invention under "high flow" conditions, when substantial "eddy currents" are present, and the resulting "dead zone".
Figure 15:
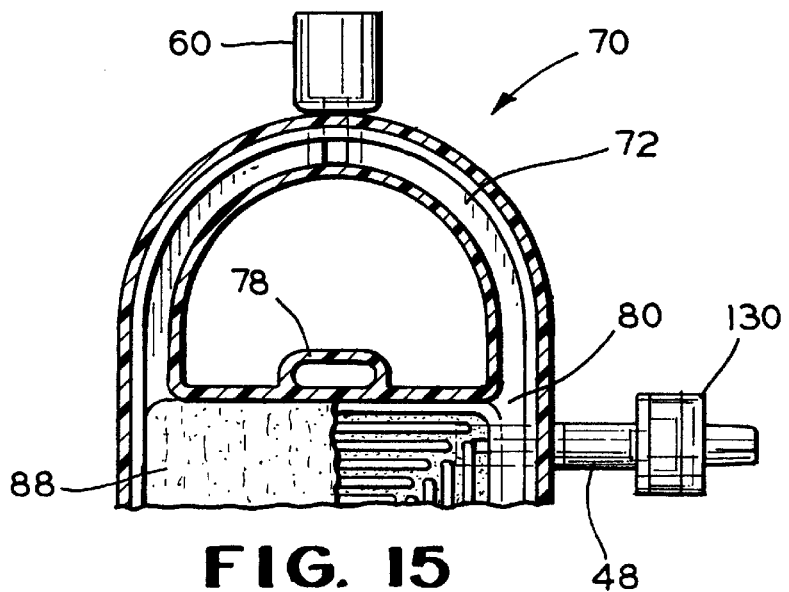
FIG. 15 is a partial sectional view of an alternative embodiment of the invention depicting a U-shaped fluid passage.
Figure 16:
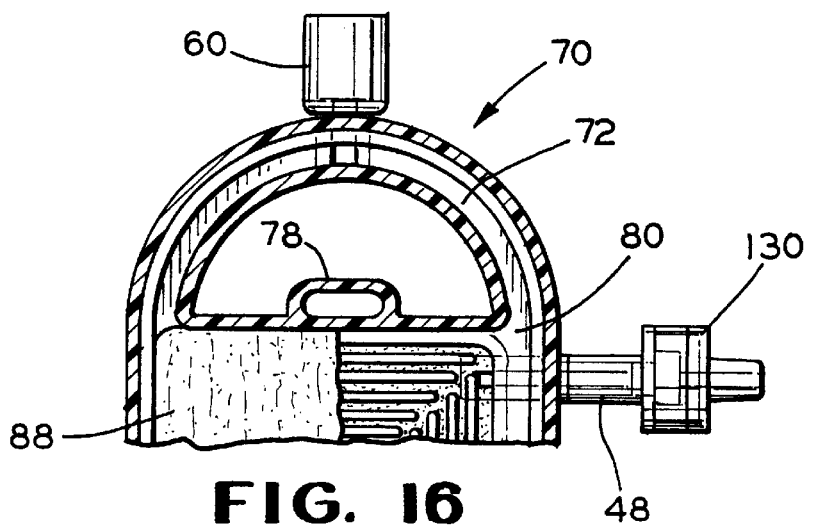
FIG. 16 is a partial sectional view of an alternative embodiment of the invention depicting a circular fluid passage.
Figure 17:
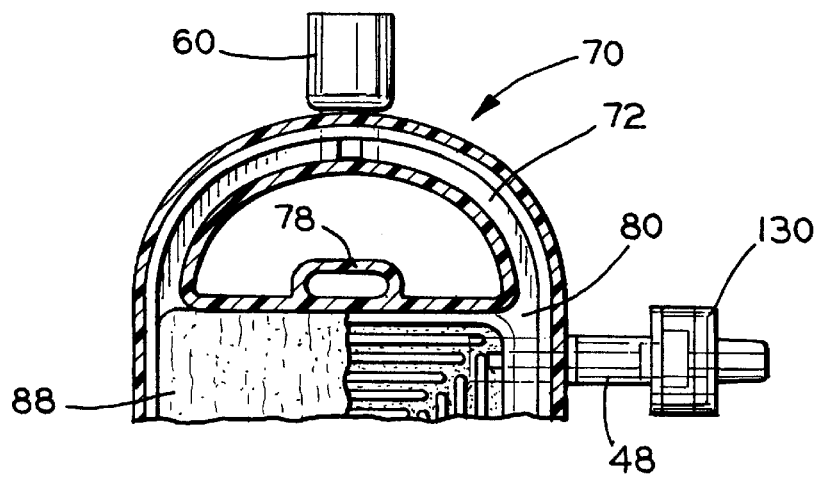
FIG. 17 is a partial sectional view of an alternative embodiment of the invention depicting a elliptical fluid passage.

Referring to FIGS. 13 and 14, it is preferred, but not necessary, that all embodiments of the high flow separation device 36 have a dead zone 102 in the first chamber 82 created by the fluid flow through the inlet 60, through passages 66, and into first chamber 82. The dead zone facilitates the passage of gas through the barrier 88.

Referring to FIG. 13., a "low flow" condition is diagrammatically shown. Low flow is to be understood to mean a flow rate through the separation device 36 where no significant "eddy currents" are formed. Under such conditions, the fluid will flow through the passages 66, spread out along sloped portion 100 of front wall 56, and will remain attached to, or reattach itself to the side walls (90,92). The flow will converge at the location labeled 150, and flow out the outlet 140. Because of the sizing of the outlet 140, fluid will flow out of the first chamber slightly slower that it will flow into it. Thus, first chamber will be full during operation. However, because the flow will be as depicted by the flow lines 152, a dead zone is created as shown at 102.

Under "high flow" conditions, which may be defined as flow through the high flow separation device 36 wherein substantial "eddy currents" 154 are present, as diagrammatically shown in FIG. 14. The "dead zone" 102 will be smaller, but the "eddy currents" will aid in causing any bubbles present to rise in the first chamber 82, and exit through the membrane 88.

As best seen from FIG. 3, proximate the down standing walls 68 and the inlet end 64, a male engagement portion 76 extends substantially vertically from the second wall 58 toward the first wall 56. A corresponding female engagement portion 78 is integrally formed within the above described down standing wall portion 68 of the first wall 56. The male portion 76 engages the female portion 78 to assist in aligning the fluid passages 66 and the first 56 and second walls 58 upon their engagement (described below). The male and female engagement portions 76, 78 are substantially the same for the elliptical inlet end 70 embodiment of the high flow separation device 36. It should be understood that the male and female engagement portions are helpful, but not necessary, to the practice of the present invention.

Fluid flows within the passages 66 until reaching a passage outlet 80. Preferably, each passage 66 has its own individual outlet 80. The outlets 80 of the individual passages communicate the fluid from the passages 66 into a first chamber 82. The passage outlets 80 are positioned to substantially direct the fluid to two distinct edge portions 84, 86 of a barrier 88, preferably adjacent at least two side walls 90, 92 within the first chamber 82 (FIGS. 2–4). It is preferred to prevent possible permanent gas entrapment in the first chamber 82, and therefore, it is desirable to place the barrier or membrane 88 as high as possible within the first chamber 82.

The side walls, generally depicted as 90, 92, are attached to the first wall 56 and second wall 58 in a substantially perpendicular relationship to the first wall 56 and second wall 58. In the preferred embodiment, the side wall 94 attached to the second wall 58 has a tongue portion 96 for sealingly connecting with a groove portion 98 mounted to the first wall 56 (FIG. 3). The first 56 and second walls 58 are connected by fitting the tongue portion 96 of the second wall 58 into the groove portion 98 of the first wall 56. In the most preferred embodiment, the first wall 56 and second wall 58 are sonically welded to secure them in a fluid tight relationship. Although the preceding description is in terms of the second wall 58 having a tongue portion 96 and the first wall 56 having a groove portion 98, it may be readily understood by those skilled in the art that the tongue portion 96 may be mounted to the first wall 56 and the groove portion 98 may be mounted to the second wall 58 without departing from the scope or spirit of the invention.

The first wall 56 and second wall 58 attached in the manner described above substantially creates the first chamber 82. Proximate the inlet end of the chamber 82, the first wall 56 is preferably biased away from the second wall 58 in the direction of fluid flow. In the most preferred embodiment, the first wall 56 is gradually sloped away from the second wall 58 in the direction of fluid flow.

Providing a sloped wall as described above serves two functions. First, as the fluid being processed exits passages 66 at passage outlets 80, the fluid stream will expand in width and depth as it flows down sloped wall portion 100, and the side wall (90 or 92) increases in area. This will slow down the flow of fluid being processed, and enable it to make a smooth transition to the maximum depth of the first chamber 82, while remaining attached, or reattaching itself, to the side walls. The design of the passages 66, side walls (90,92) and sloped portion should be chosen such that fluid will attach itself to the walls of the passages 66, and remain attached, or reattach itself easily, to the side walls (90,92) as it flows into first chamber 82. A discussion of the conditions necessary are discussed at page 241 "Jet Reattachment and the Coanda Effect" of the chapter entitled "Jets, Plumes, Wakes, and Shear Layers", from the Applied Fluid Dynamics Handbook, Krieger Publishing Co. (1992).

Secondly, the decreasing cross sectional area of the first chamber 82 in the direction opposite of the fluid flow, which is the direction any entrapped or entrained gasses will be flowing, aids and encourages gas flow across and through the porous barrier 88.

A second chamber 104 is preferably located adjacent the first chamber 82. In the most preferred embodiment, the second chamber 104 is integrally formed with the second wall 58 of the first chamber 82. The second chamber 104 may extend substantially the width of the first chamber 82.

The second chamber 104 has a plurality of interconnected channels 106 which substantially span the length and width of the second chamber 104. The channels 106 may have a plurality of orientations and designs. In the preferred embodiment, the channels 106 are oriented in substantially four quadrants, generally designated as 108, 110, 112, 114 (see FIG. 3). The channels 106 within the first 108 and second 110 quadrants are preferably oriented substantially perpendicular to the direction of fluid flow. The channels 106 within the third 112 and fourth 114 quadrants are preferably oriented substantially parallel to the direction of flow.

In the preferred embodiment, a hydrophobic porous barrier 88 completely covers and substantially separates the first chamber 82 from the second chamber 104. As depicted in FIG. 3, the barrier 88 has a top edge 116, a bottom edge 118, a right 120 and left side edge 122, and a center portion 124. The top edge 116 of the barrier 88 is attached adjacent the fluid outlets 80. The right 120 and left 122 side edges are attached adjacent the side walls 94.

The barrier 88 may consist of one or more layers and may be made of a wide variety of materials known in the art. At least the layer which contacts the fluid being processed should be hydrophobic, i.e., not wetted by the fluid being processed. Any hydrophobic material which prohibits the fluid being processed from passing through the membrane could be used.

Preferably, the barrier 88 will also act as a bacteria retention material capable of preventing bacteria from entering the system through the vent 48. This may be accomplished at least by choosing the pore size of the fluid contacting layer of the barrier 88 such that the bacteria can not pass through the pores. In the preferred embodiment, the barrier 88 has a pore size of approximately 0.2 microns. The barrier will be made of a synthetic fluorine containing resin or polypropelene, and will have a backing support 126 integrally formed with the barrier 88 to prevent the barrier 88 from splitting or rupturing during use. The backing support 126 may be formed, attached, or placed between the barrier 88 and the second wall 58. A seal located around the entire perimeter 116, 118, 120,122 of the barrier 88 bonds the barrier 88 to the second wall 58. The seal 128 may be a heat seal, sonic seal, adhesive seal, or any other air-tight seal. The seal 128 (FIG. 2) prohibits fluid by-passing the barrier 88 and entering the second chamber 104, and air or gas in the second chamber 104 from entering into the first chamber 82.

In the alternative embodiment wherein a plurality of passages connect the inlet 60 to the first chamber 82, an individual barrier may be located proximate each passage outlet (not shown). Each barrier 88 is attached, as described above, to the second wall 58, however, it is located substantially between each outlet 80. Additionally, each barrier 88 is in communication with the second chamber 104, also as described above.

Figure 6:
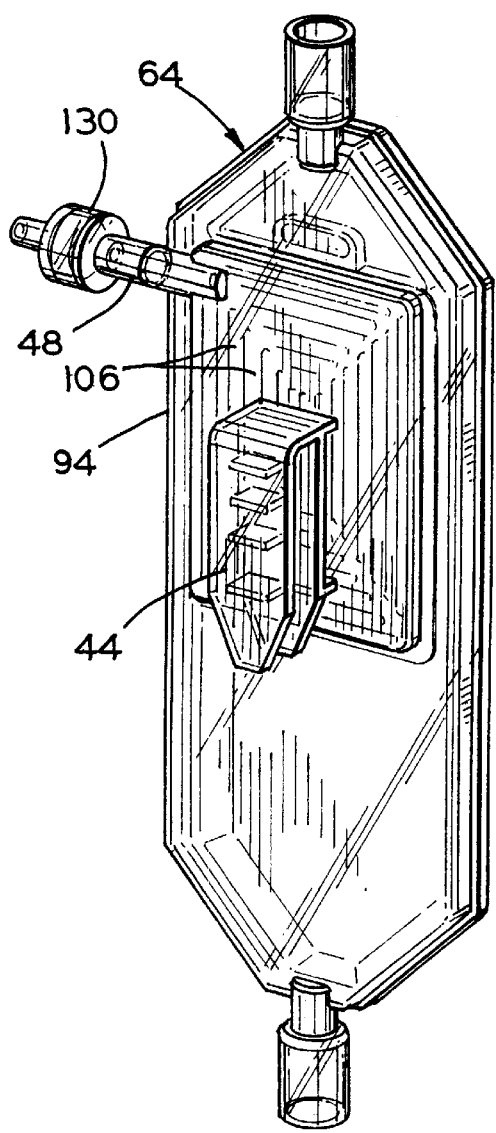
FIG. 6 shows a modification of the construction shown in FIG. 2 having a faceted fluid passage with a back-mounted attachment clip.
Figure 7:
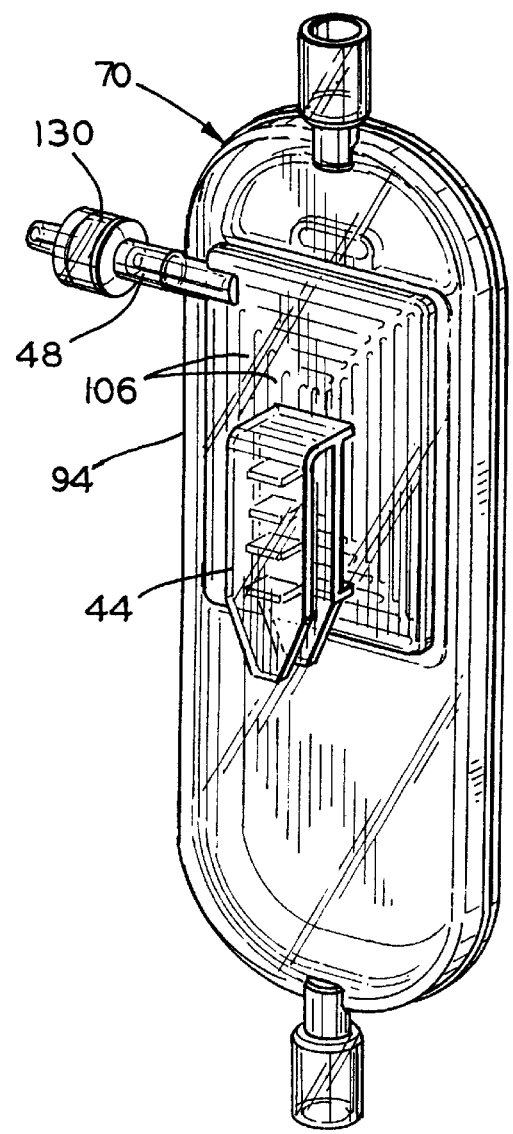
FIG. 7 shows a modification of the construction shown in FIG. 3 having an elliptical fluid passage and a back-mounted attachment clip.

As depicted in FIGS. 6–7, a vent 48, in fluid communication with the channels 106, allows air or gas collected by the channels 106 to escape. In the embodiments of FIGS. 6 and 7, the vent 48 is located proximate the inlet end 64, 70 on one of the side walls 94. The vent 48 is a tubular design for fluid communication with surgical tubing, or the like. In this embodiment, a check valve 130 may be connected in series downstream from the vent 48 to prevent gas or air re-introduction to the fluid through the barrier 88.

In an alternative embodiment, depicted in FIGS. 8–12, a vent 132 is a fluid connection between said channels 106 and a one way diaphragm 134 attached to a main wall 136 of the second chamber 104. The diaphragm 134 is in fluid communication with the channels 106 through the main wall 136 of the second chamber main wall 136, thereby allowing air or gas collected within the channels 106 to escape through the diaphragm 134. At least one protective upstanding wall 138 extends from the main wall 136 and substantially surrounds the diaphragm vent 134 to protect it during use.

A fluid outlet 140 is located at the outlet end 142 of the first chamber 82. The outlet 140 is integrally formed with the second wall 58 and acts to communicate fluids from the first chamber 82 to a patient 40. The outlet 140 is sized to provide sufficient back pressure against the barrier 88 to prevent gas re-introduction through the barrier 88. In an alternative embodiment, a plurality of outlets are integrally formed with the second wall 58 (not shown). The outlets allow for a greater volume of filtered fluid to exit the invention and be transported to an awaiting patient 40.

In an alternative embodiment, a barrier is placed in first chamber, at or near the outlet 140 to prevent any residual air or gas bubbles from escaping (not shown). In this embodiment, the barrier is placed across the opening of the outlet 140, in first chamber 82, and is secured anywhere between passage outlets 80 and the outlet 140. The barrier may be secured by a heat seal, adhesive seal, sonic welded seal, or any other air-tight seal. The barrier 140 is preferably a porous media screen with sufficient pore size to block gas from exiting, but not small enough to get plugged, or remove fluid components. In embodiments wherein a plurality of outlets are employed, a barrier corresponding to each outlet may be secured across the outlet 140 in the manner described above.

Figure 11:
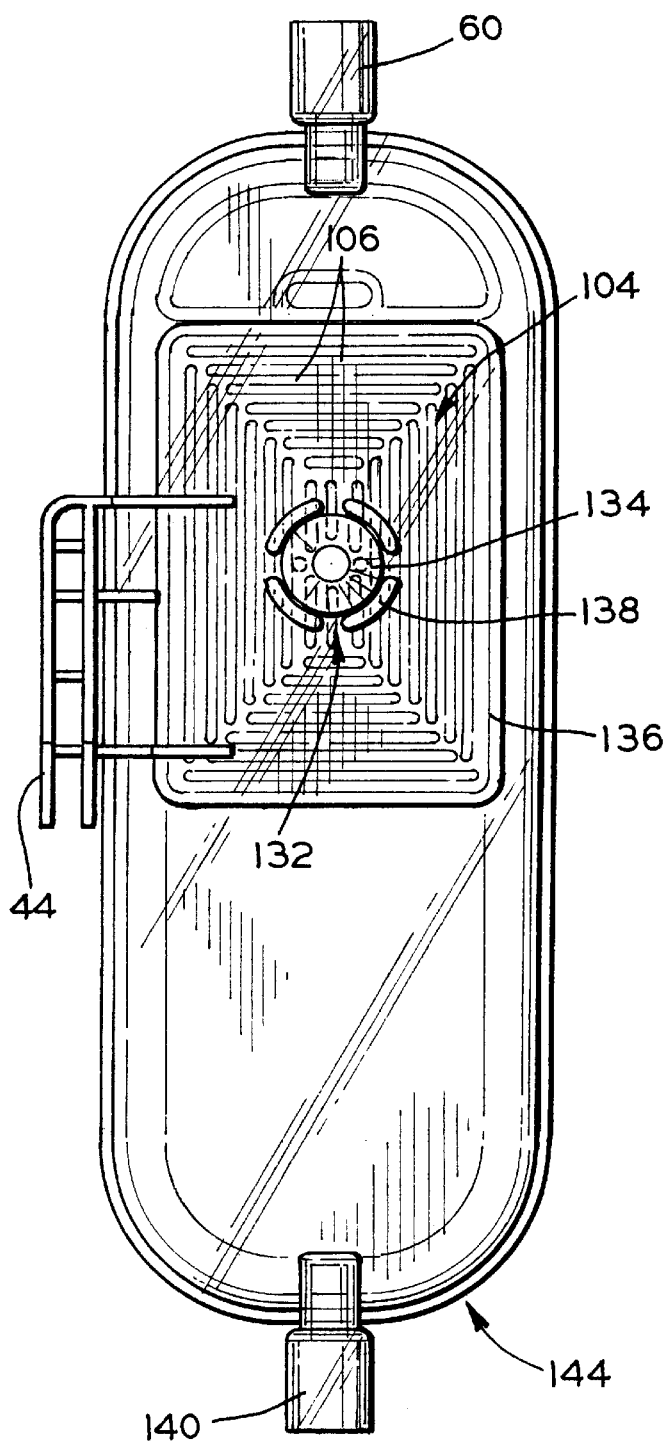
FIG. 11 shows a modification of the construction shown in FIG. 1 but having a diaphragm vent.
Figure 12:
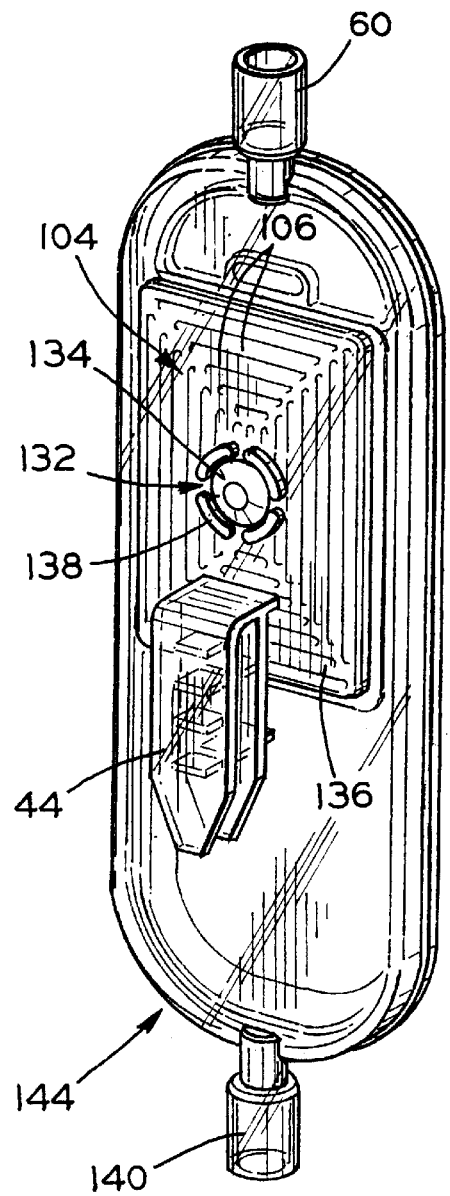
FIG. 12 is a view, similar in part to FIG. 11, but having the attachment clip located on the second wall below the diaphragm vent.

The outlet 140 is integrally formed with a multi-faceted, or multi-surfaced, outlet end 142. (FIGS. 8–9). Each of the facets is an angled flow surface designed to direct outgoing fluid into the outlet 140. In an alternative embodiment, the outlet end 142 is substantially elliptical. (FIGS. 11–12). The outlet end 144 may also be elliptical, parabolic or U-shaped to correspond with the shape of the inlet end 70.

FIGS. 6–7, 9 and 12 depict an alternative embodiment for attaching the high flow separation device 36 to adjacent equipment 42. In this embodiment, the clip 44 described above is secured to the main wall 136 of the second chamber 104. As shown in FIG. 9, the clip 44 may be located on the main wall 136 below the diaphragm vent 134 to avoid interference with the vent 134. It may be understood by those skilled in the art that the clip 44 may be located on any surface of the high flow separation device 36 which does not interfere with the function of the high flow separation device 36 and securely maintains the high flow separation device 36 in a substantially upright attitude for use.

The following is a detailed description of the operation of the high flow separation device 36. A fluid source 22 containing fluid is attached to a pressure infusion system 20. The pressure infusion system 20 pressurizes the unprocessed fluid, thereby moving it from the fluid source 22 to a drip chamber microaggregate 26. The microaggregate 26 removes blood clots and the like from the fluid before the fluid is transported to a fluid warming system 32. The fluid warming system 32 warms intravenous fluids before they are delivered to the patient 40.

The fluid is transported from the warming system 32 to at least one inlet 60 located on the inlet end 64, 70 of the high flow separation device 36. The fluid passes through the inlet 60 and is split and redirected into at least one passage 66, 72. The majority of fluid flows into the passage 66, 72 and then into the first chamber 82. A small amount of fluid, however, may flow under the down standing wall 68 and then into the first chamber 82.

In the preferred embodiment, the passages 66, 72 terminate adjacent the top edge portion 116 of the barrier material 88 and proximate the side walls 90, 92 of the first chamber 82. The fluid flows substantially down the side walls 90, 92 of the first chamber 82, which begins to fill. Directing the fluid to the side walls 90, 92 of the first chamber 82 slows the fluid as it is being introduced into the first chamber 82.

Directing the fluid to the side walls 90, 92 of the chamber also substantially reduces fluid motion in the center portion 124 of the barrier 88. Fluid flowing in the center portion 124 of the barrier 88 begins to flow across the surface of the barrier 88.

The fluid continues to enter the chamber 82 primarily along the side walls 90, 92 thereby leaving a fluid dead zone 102 located substantially adjacent the barrier 88, and more specifically, adjacent the center portion 124 of the barrier 88. The fluid dead zone 102 is a fluid zone of relatively little motion. Bubbles which enter the chamber 82 tend to move away from the incoming fluid at the side walls 90, 92 and move toward the fluid dead zone 102. The relatively calm nature of the dead zone 102 assists the bubbles to coalesce within this zone 102. The laminar flow within this zone 102 also increases the effectiveness of the venting capability of the porous barrier 88.

The slope 100 of the first wall 56 away from the second wall 58 in the direction of the fluid flow acts to increase the cross sectional area of the first chamber 82 proximate the barrier 88. The increase in cross sectional area contributes to the relative calm nature of the fluid in the dead zone 102 and, also assists the air or gas to coalesce.

The barrier 88 is located adjacent the fluid dead zone 102. The hydrophobic nature of the barrier 88 allows the bubbles which have coalesced adjacent the barrier 88 to pass through the barrier 88, yet the barrier 99 prohibits the fluid from escaping. The air or gas pass through the barrier 88 and are captured by the plurality of channels 106 within the second chamber 104. The air or gas then move toward either of the two vents 48, 134 described above for discharge from the high flow separation device 36.

In the alternative embodiment wherein a plurality of passages connect the inlet 60 to the first chamber 82, and an individual barrier is located proximate each passage outlet 80, a fluid dead zone is created adjacent each barrier substantially between the passages (not shown). Bubbles which have coalesced from the fluid collect in one of the dead zones where they pass through the barrier and into the second chamber 104.

The filtered fluid moves toward the outlet end 142, 144 of the high flow separation device 36. In one embodiment of the high flow separation device 36, the fluid may pass through a second barrier located at the outlet end 142, 144 of the high flow separation device 36. Whether passed through a second barrier or not, the fluid passes through at least one outlet 140 to be delivered to the patient 40. The size of the outlet 140 provides a sufficient back pressure against the barrier 88 to assist in preventing re-introduction of air or gas into the fluid, and effectively vents gas out of the device.

In accordance with the provisions of the patent statutes, the present invention has been described in what is considered to represent its preferred embodiment, however, it should be noted that the invention can be practiced otherwise than as specifically illustrated and described without departing from its scope or spirit.

What is claimed is:

1. A method for removing entrained air or gas from fluids, comprising:
   communicating a fluid from at least one fluid inlet to at least one side wall within a first chamber;
   creating a fluid dead zone within said first chamber, and filtering air or gas entrained in said fluid through a barrier adjacent said fluid dead zone into a second chamber.

2. The method defined in claim 1, and including the further step of,
   venting said air or gas from said second chamber.

3. A method for removing entrained air or gas from fluids as defined in claim 1, further comprising diverting an inlet flow through at least one fluid passage to said first chamber.

4. A method for removing entrained air or gas from fluids as defined in claim 3, further comprising diverting an inlet flow through at least two fluid passages to said first chamber.

5. A method for removing entrained air or gas from fluids as defined in claim 3, further comprising terminating said fluid passage adjacent said side wall.

6. A method for removing entrained air or gas from fluids as defined in claim 3, further comprising terminating said fluid passages adjacent said at least one side wall.

7. A method for removing entrained air or gas from fluids as defined in claim 1, further comprising communicating said fluid along said at least one side wall to substantially prevent splashing.

8. A method for removing entrained air or gas from fluids as defined in claim 1, further comprising communicating said fluid along said at least one side wall to minimize bubble generation.

9. A method for removing entrained air or gas from fluids as defined in claim 1, further comprising communicating said fluid along said at least one side wall to promote bubble migration toward the barrier.

10. A method for removing entrained air or gas from fluids as defined in claim 1, further comprising communicating said fluid along said at least one side wall to reduce fluid velocity in the main fluid flow direction.

11. A method for removing entrained air or gas from fluids as defined in claim 1, further comprising raising the level of said fluid in said first chamber to coalesce air or gas proximate a barrier.

12. A method for removing entrained air or gas from fluids as defined in claim 1, further comprising reducing the volume of said first chamber proximate said barrier.

13. A method for removing entrained air or gas from fluids as defined in claim 1, further comprising creating a fluid dead zone proximate said barrier to enable said air or gas to coalesce and to assist said coalesced air or gas to pass through said barrier.

14. A method for removing entrained air or gas from fluids as defined in claim 1, further comprising filtering said coalesced air or gas from said fluid dead zone to a second chamber.

15. A method for removing entrained air or gas from fluids as defined in claim 1, further comprising collecting said transferred air or gas in a plurality of channels behind said barrier.

16. A method for removing entrained air or gas from fluids as defined in claim 1, further comprising venting said collected air or gas.

17. A method for removing entrained air or gas from fluids as defined in claim 1, further comprising preventing re-introduction of air or gas through said barrier by locating a check valve down stream of said barrier.

18. A method for removing entrained air or gas from fluids as defined in claim 1, further comprising preventing re-introduction of air or gas through said barrier by sizing an outlet to create back pressure against said barrier.

19. A bubble trap for fluids, including:
   a) a first chamber, including:
      1) a first wall portion, including:
         a) an inlet end,
         b) a plurality of sidewalls down standing from said first wall,
         c) a plurality of down standing walls proximate said inlet end,
         d) a portion of said first wall proximate said plurality of down standing walls biased toward said first wall portion, and
         e) an outlet end, and
      2) a second wall portion, including:
         a) an inlet end,
         b) a fluid inlet integrally formed within said inlet end,
         c) a plurality of side walls upstanding from said second wall,
         d) an outlet end, and
         e) a fluid outlet integrally formed in said outlet end, and
   b) a second chamber adjacent said first chamber, including:
      1) plurality of interconnected channels, and c) at least one porous barrier separating said first chamber from said second chamber.

20. A device for removing entrained air or gas from fluids, comprising:
a first chamber having at least one fluid inlet, at least one fluid outlet; and at least one sidewall,
a second chamber adjacent said first chamber having a plurality of interconnected channels;
at least one porous barrier attached to said first chamber and separating said first chamber and said second chamber;
at least one fluid passage in communication with said inlet and terminating in said first chamber adjacent said at least one side wall.

21. A device for removing entrained air or gas from fluids, comprising:
a first chamber having at least one fluid inlet, at least one fluid outlet; and at least one sidewall,
a second chamber adjacent said first chamber having a plurality of interconnected channels;
at least one porous barrier attached to said first chamber and separating said first chamber and said second chamber;
at least one fluid passage in communication with said inlet and terminating in said first chamber adjacent said at least one side wall, and
a vent in fluid communication with said channels.

22. A device for removing entrained air or gas from fluids as defined in claim 20, further comprising at least two fluid passages in communication with said inlet and each of said fluid passages terminating adjacent a distinct edge portion of said barrier different from said edge portion at which the other of said at least two passages terminated.

23. A device for removing entrained air or gas from fluids as defined in claim 22, further comprising said first chamber having a first wall and a second wall maintained in a substantially parallel, spaced-apart relationship by a plurality of upstanding side walls securely attached to said first and said second walls.

24. A device for removing entrained air or gas from fluids as defined in claim 23, further comprising said inlet and said outlet being integrally formed with said second wall.

25. A device for removing entrained air or gas from fluids as defined in claim 24, further comprising said inlet and said outlet integrally formed with said first wall.

26. A device for removing entrained air or gas from fluids as defined in claim 25, further comprising said first and second walls each having an inlet end and an outlet end.

27. A device for removing entrained air or gas from fluids as defined in claim 26, further comprising said inlet end and said outlet end are rounded.

28. A device for removing entrained air or gas from fluids as defined in claim 26, further comprising said inlet end and said outlet end are multi-faceted.

29. A device for removing entrained air or gas from fluids as defined in claim 26, further comprising said inlet end and said outlet end are oval.

30. A device for removing entrained air or gas from fluids as defined in claim 26, further comprising said inlet end and said outlet end are U-shaped.

31. A device for removing entrained air or gas from fluids as defined in claim 26, further comprising said inlet end and said outlet end are elliptical.

32. A device for removing entrained air or gas from fluids as defined in claim 25, further comprising said passages formed by said first wall having a down standing portion, said down standing portion formed in a parallel, spaced-apart relationship with said inlet end.

33. A device for removing entrained air or gas from fluids as defined in claim 32, further comprising said down standing portion substantially directing said fluid into said passages.

34. A device for removing entrained air or gas from fluids as defined in claim 33, further comprising said passages formed by said second wall having an upstanding portion, said upstanding portion formed in a parallel, spaced-apart relationship with said inlet end.

35. A device for removing entrained air or gas from fluids as defined in claim 34, further comprising said upstanding portion substantially directing said fluid into said passages.

36. A device for removing entrained air or gas from fluids as defined in claim 35, further comprising a male engagement portion securely attached to said first wall proximate said inlet end.

37. A device for removing entrained air or gas from fluids as defined in claim 36, further comprising a female engagement portion securely attached to said second wall proximate said inlet end.

38. A device for removing entrained air or gas from fluids as defined in claim 37, further comprising a fluid dead zone located proximate said barrier.

39. A device for removing entrained air or gas from fluids as defined in claim 38, further comprising said fluid dead zone located substantially between said side walls and adjacent said barrier.

40. A device for removing entrained air or gas from fluids as defined in claim 39, further comprising said side walls of said first wall having a tongue portion and said side walls of said second wall having a groove portion, said tongue and groove portions combine to seal said first and said second walls in a spaced-apart relationship.

41. A device for removing entrained air or gas from fluids as defined in claim 40, further comprising said side walls of said first and second walls sonically welded together.

42. A device for removing entrained air or gas from fluids as defined in claim 41, further comprising said first wall biased toward said second wall proximate said inlet end.

43. A device for removing entrained air or gas from fluids as defined in claim 42, further comprising said passages terminating adjacent said side wall.

44. A device for removing entrained air or gas from fluids as defined in claim 43, further comprising said barrier being a hydrophobic porous barrier with backing support.

45. A device for removing entrained air or gas from fluids as defined in claim 44, further comprising said barrier is a bacteria retention material.

46. A device for removing entrained air or gas from fluids as defined in claim 45, further comprising said barrier is approximately 0.2 microns thick.

47. A device for removing entrained air or gas from fluids as defined in claim 46, further comprising said second chamber integrally formed with said second wall.

48. A device for removing entrained air or gas from fluids as defined in claim 47, further comprising said vent located proximate said inlet end on a side wall.

49. A device for removing entrained air or gas from fluids as defined in claim 48, further comprising a check valve located downstream of said vent to prevent gas re-introduction into said fluid through said barrier.

50. A device for removing entrained air or gas from fluids as defined in claim 49, further comprising said outlet sized to provide sufficient back pressure against said barrier to prevent gas re-introduction through said barrier.

51. A device for removing entrained air or gas from fluids as defined in claim 50, further comprising an attachment means for securely attaching, and maintain in an upright position, said device.

52. A device for removing entrained air or gas from fluids as defined in claim 51, further comprising said attachment means is a clip located on a side wall of said first wall.

53. A device for removing entrained air or gas from fluids as defined in claim 52, wherein said attachment means is a clip attached to said second chamber.

54. A device for removing entrained air or gas from fluids as defined in claim 53, further comprising said vent is a fluid connection between said channels and a one way diaphragm attached to said second chamber.

55. In a pressure infusion system, a device for removing entrained gas from fluids comprising:

A device for removing entrained air or gas from fluids, comprising:
- a first chamber having at least one fluid inlet and at least one outlet;
- a second chamber adjacent said first chamber having a plurality of interconnected channels;
- at least one porous barrier separating said first chamber and said second chamber;
- at least one fluid passage in communication with said inlet and terminating in said first chamber adjacent an edge portion of said barrier; and
- a vent in fluid communication with said channels.

56. In a blood warming system, a device for removing entrained gases from blood comprising:

A device for removing entrained air or gas from fluids, comprising:
- a first chamber having at least one fluid inlet and at least one outlet;
- a second chamber adjacent said first chamber having a plurality of interconnected channels;
- at least one porous barrier separating said first chamber and said second chamber;
- at least one fluid passage in communication with said inlet and terminating in said first chamber along an edge portion of said barrier; and
- a vent in fluid communication with said channels.

57. A system for removing entrained air or gas from intravenous fluids, comprising:
- a pressure infusion system in fluid communication with an intravenous fluid source;
- a fluid warming device in fluid communication with said pressure infusion system;
- a bubble trap in fluid communication with said fluid warming device; said bubble trap comprising:
  - a first chamber having at least one fluid inlet and at least one outlet;
  - a second chamber adjacent said first chamber having a plurality of interconnected channels;
  - at least one porous barrier separating said first chamber and said second chamber;
  - at least one fluid passage in communication with said inlet and terminating in said first chamber along an edge portion of said barrier; and
  - a vent in fluid communication with said channels: and
- a fluid connection between said bubble trap and a fluid recipient.

* * * * *